United States Patent
Kokic et al.

(10) Patent No.: US 9,436,924 B2
(45) Date of Patent: Sep. 6, 2016

(54) AUTOMATED ANALYTE SENSOR ORDERING METHODS AND APPARATUS

(71) Applicant: Bayer HealthCare LLC, Tarrytown, NY (US)

(72) Inventors: Mirza Kokic, New York, NY (US); John Farrell, Wyomissing, PA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 50 days.

(21) Appl. No.: 13/707,112

(22) Filed: Dec. 6, 2012

(65) Prior Publication Data

US 2014/0161667 A1 Jun. 12, 2014

(51) Int. Cl.
*G06Q 10/08* (2012.01)
*G06Q 50/22* (2012.01)
*G06F 19/00* (2011.01)
*G01N 33/487* (2006.01)
*G01N 27/327* (2006.01)

(52) U.S. Cl.
CPC ........ *G06Q 10/087* (2013.01); *G01N 33/4875* (2013.01); *G06F 19/327* (2013.01); *G06Q 50/22* (2013.01); *G01N 27/3272* (2013.01)

(58) Field of Classification Search
CPC .............. G06Q 10/087; G06Q 50/22; G01N 33/4875; G01N 27/3272; G06F 19/327
USPC ......... 700/266; 702/19, 22, 30, 31; 422/430, 422/68.1
See application file for complete search history.

(56) References Cited

U.S. PATENT DOCUMENTS

| | | | |
|---|---|---|---|
| 6,295,506 B1* | 9/2001 | Heinonen et al. | 702/104 |
| 6,413,213 B1* | 7/2002 | Essenpreis et al. | 600/300 |
| 6,494,830 B1 | 12/2002 | Wessel | |
| 6,699,188 B2 | 3/2004 | Wessel | |
| 2003/0050537 A1* | 3/2003 | Wessel | A61B 5/04325 600/300 |
| 2006/0292039 A1* | 12/2006 | Iida | 422/82.05 |
| 2008/0294024 A1* | 11/2008 | Cosentino | A61B 5/14532 600/309 |
| 2013/0116526 A1* | 5/2013 | Javitt | A61B 5/14532 600/365 |

* cited by examiner

Primary Examiner — Shogo Sasaki
(74) Attorney, Agent, or Firm — Dugan & Dugan, PC

(57) ABSTRACT

Methods, systems, and apparatus adapted to automate ordering of test strips for use in an analyte meter device are disclosed. The method, system and apparatus includes inputting information from an indicia on a package of test strips indicative of a quantity of test strips in the package; tracking a number of test strips used in the analyte meter device; and generating an automatic order for additional test strips based on a signal indicating that a reorder threshold has been reached. Numerous additional features and aspects are disclosed.

6 Claims, 4 Drawing Sheets

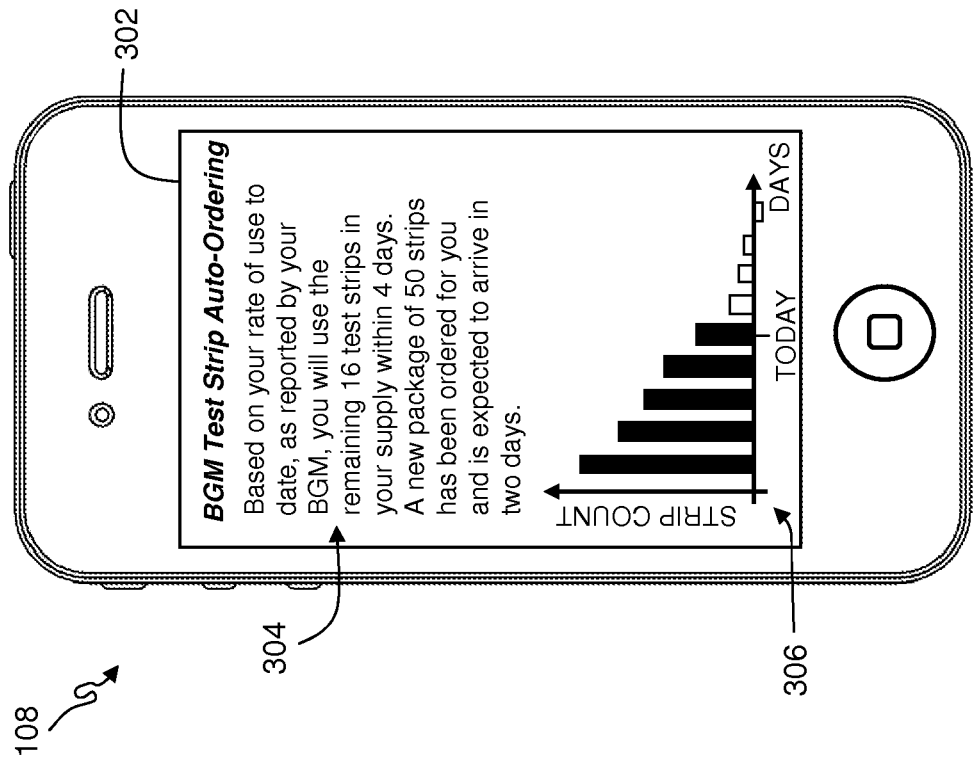
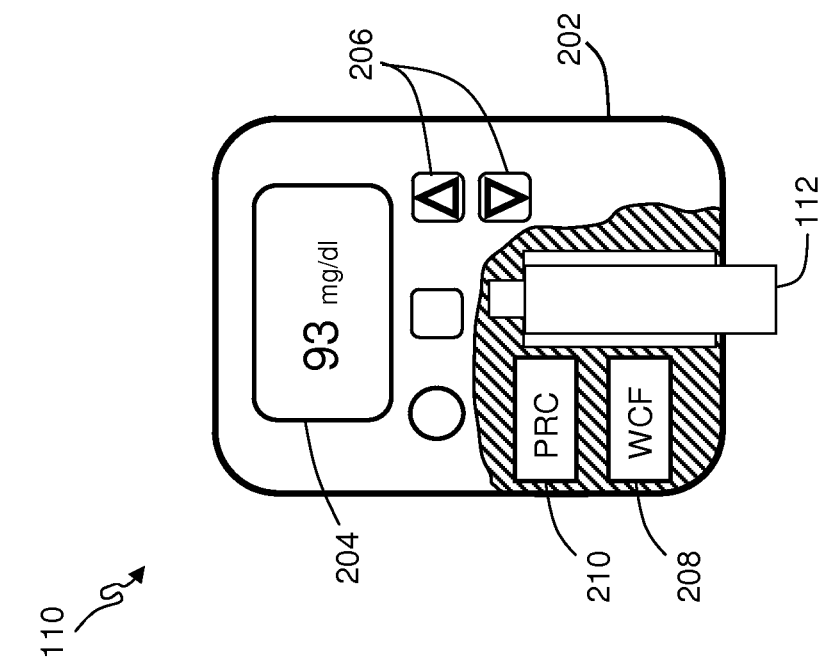
FIG. 3
FIG. 2

| TEST ID 402 | TEST DATE 404 | TEST TIME 406 | TEST RESULT 408 | REMAINING STRIP COUNT 410 | CONSUMPTION RATE 412 | ANTICIPATED REORDER DATE 414 |
|---|---|---|---|---|---|---|
| 2043 | 5/1/12 | 4:09PM | 93 mg/dl | 17 | 4.1/day | 5/2/12 |
| 2044 | 5/1/12 | 8:22PM | 89 mg/dl | 16 | 4/day | 5/2/12 |
| 2045 | 5/2/12 | 7:15AM | 74 mg/dl | 15 | 4/day | 5/17/12 |
| ... | | | | | | |
| 2052 | 5/4/12 | 7:02AM | 85 mg/dl | 8 | 4/day | 5/17/12 |
| 2053 | 5/4/12 | 11:11AM | 82 mg/dl | 57 | 4/day | 5/17/12 |

*FIG. 4*

AUTOMATED ANALYTE SENSOR ORDERING METHODS AND APPARATUS

BACKGROUND

The present invention relates to automated methods and apparatus for ordering analyte sensors that are used to detect an analyte characteristic in a fluid sample.

The monitoring of analyte concentration levels or other properties in a biological fluid can be used for health diagnostics. For example, an analyte sensor (more generally known a "test strip") can be employed to monitor a patient's blood glucose level as part of diabetes treatment and care. Furthermore, test strips can be used to detect or measure concentrations of other analytes, such as lactate, keytones, total cholesterol, uric acid, lipids, triglycerides, high-density lipoprotein (HDL), low-density lipoprotein (LDL), hemoglobin A1c, etc.

A disposable single-use test strip is used to detect an analyte concentration level in a biological fluid sample such as from a single sample of blood or other interstitial fluid. For example, the biological fluid can be obtained from the patient via a lancet (e.g., by a pinprick or needle). Typically, after a biological fluid sample has been obtained from the patient, such as by the use of a lancet, the biological fluid sample is then transferred to the test strip for measurement of the biological fluid sample's analyte concentration level using, for example, a blood glucose meter (BGM) or other analyte meter device (AMD). Application of the biological fluid to the test strip initiates a reaction that consumes the reactants (e.g., catalytic agents or reagents such as oxidase enzymes) on the strip and the strip cannot be used again. Thus, once the analyte concentration has been measured, the test strip is disposed. Therefore, each use of a BGM requires the consumption of a test strip. Typically, test strips are purchased in a package of fifty (50) and the lot is labeled with an assigned identifier and an expiration date. Once the user begins to run low on their test strip supply, the user typically must remember to order, or go to a store to purchase, additional strips. If the user fails to get additional strips in time, the user will not be able to use the BGM or other analyte meter device. Because the strips expire, maintaining a large supply of strips results in waste if not used before expiration.

Accordingly, there is a need for timely automated test strip ordering methods and apparatus that ensure users of BGMs, or other analyte meter devices, have an adequate supply of test strips that will not expire before the strips are needed and used.

SUMMARY

In some embodiments, the present invention provides a method of ordering test strips for an analyte meter device. The method includes inputting information from an indicia on a package of test strips indicative of a quantity of test strips in the package; tracking a number of test strips used in the analyte meter device; and generating an automatic order for additional test strips based on a signal indicating that a reorder threshold has been reached.

In some other embodiments, the present invention provides an automated analyte meter test strip ordering system. The system includes an analyte meter device adapted to use test strips to measure a characteristic of an analyte; and a personal communications device adapted to input information from an indicia on a package of test strips, adapted to communicate with the analyte meter device, and adapted to order test strips based on information received from the analyte meter device.

In yet other embodiments, the present invention provides an analyte meter device. The device includes a test strip port adapted to receive test strips for testing an analyte characteristic of a fluid; a processor for executing an operating program adapted to control the analyte meter device; and a communications facility adapted to allow the analyte meter device to communicate with a personal communications device to receive information input from a test strip package and to transmit test strip usage information.

In still yet other embodiments, the present invention provides a personal communications device application. The application includes processor instructions adapted to be executed on a personal communications device. The executable instructions are further adapted to control the personal communications device to input information from an indicia on a package of test strips indicative of a quantity of test strips in the package; track a number of test strips used in an analyte meter device; and generate an automatic order for additional test strips based on a determination that a reorder threshold has been reached.

These and other features of the present teachings are set forth herein. Other features and aspects of the present invention will become more fully apparent from the following detailed description, the appended claims and the accompanying drawings.

DRAWINGS

The skilled artisan will understand that the drawings, described below, are for illustration purposes only. The drawings are not intended to limit the scope of the present teachings in any way.

FIG. 2 illustrates a partially cross-sectioned top view of an embodiment of an example analyte meter device (AMD) with a test strip inserted according to embodiments.

FIG. 3 illustrates a top view of an embodiment of an example personal communication device (PCD) with a screen display according to embodiments.

FIG. 4 illustrates a table representation of an example database useful for storing test strip data according to embodiments.

DESCRIPTION OF VARIOUS EMBODIMENTS

According to some aspects of the present invention, automated ordering of analyte sensors (i.e., test strips) is achieved using a personal communications device (PCD) such as, for example, a smart phone, a tablet, or a phablet executing an application adapted to communicate with an analyte meter device (AMD) such as, for example, a blood glucose meter (BGM). In some embodiments, when a user receives an initial supply of test strips, the PCD is used to input information from an indicia (e.g., by scanning a barcode, QR code, etc.) on the packaging of the test strips into the PCD application. The indicia indicate the type, quantity, and other information about the test strips. The PCD communicates (e.g., wirelessly) the type, quantity, and other information to the AMD. As the user tests analyte properties and consumes test strips over time, the AMD tracks use of the test strips and, at an appropriate time, automatically communicates to the PCD application that additional test strips are going to be needed, or in some embodiments, should be ordered. The PCD application automatically orders the correct type and quantity of strips from a preselected or suggested supplier.

In some embodiments, a preselected remaining quantity can be used trigger the ordering of additional test strips. In some embodiments, the trigger for ordering can be based upon a predicted date that the user will need more strips or need to order more strips. The predicted date can be determined based upon available quantity, rate of use, supplier, shipping time, etc. Once the new test strips arrive, the user is directed to input information from the indicia on the packaging with the PCD (either manually or by scanning) and the process repeats.

In some embodiments, the AMD includes some of the functionality of the PCD and can be operative to be used to scan the indicia and automatically order additional test strips in addition to the above-described functions. In some embodiments, the AMD reports each use of a test strip to the PCD. In such embodiments, the PCD tracks the user's inventory of test strips and determines when to order additional test strips. These and other embodiments of automated test strip ordering systems, apparatus and methods are described below with reference to FIGS. 1 through 5.

Figure 1:
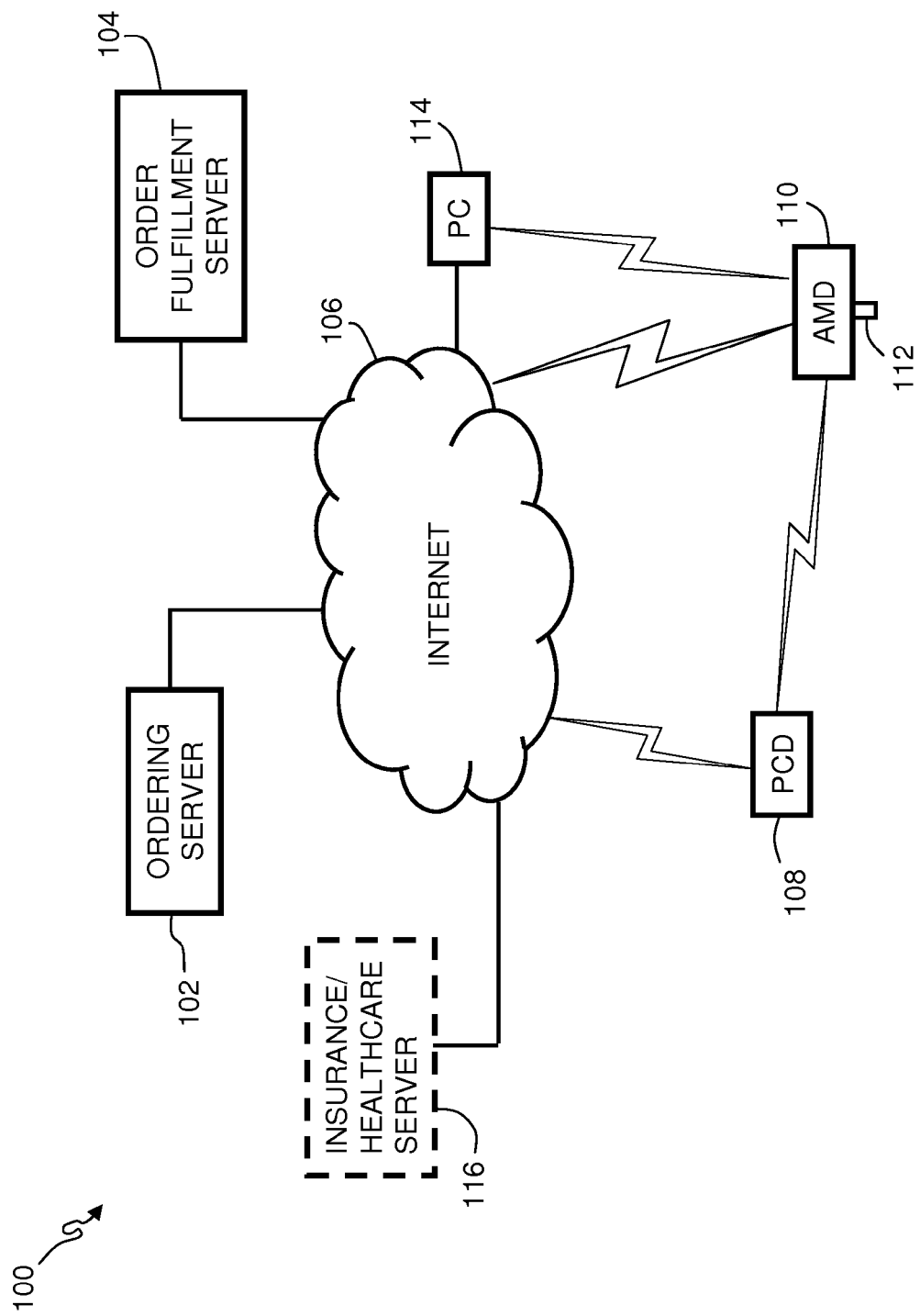
FIG. 1 illustrates a block diagram of an embodiment of an example automated test strip ordering system according to embodiments.

Turning to FIG. 1, an example embodiment of an automated test strip ordering system 100 is pictured. The system 100 includes a networked ordering server 102 that is adapted to receive orders from users and to dispatch delivery instructions to a networked order fulfillment server 104. In some embodiments, the ordering server 102 and the order fulfillment server 104 can be the same machine, can be on the same local network, and/or be operated by the same entity (e.g., a test strip manufacturer, a test strip supplier/distributer, etc.). The servers 102, 104 are coupled to, and communicate via, the Internet 106 or any other suitable, practicable network or communications system. The system 100 also includes a personal communications device (PCD) 108 such as, for example, a smart phone, a tablet, or a phablet. Examples of smart phones include the Apple® iPhone®, Motorola® Droid®, HTC® Evo®, Asus® PadFone®, ZTE® Score®, LG® Viper®, Nokia® Lumia®, Pantech® Burst®, I-Mobile® MyTouch®, Huawei® Ascend®, Sony® Ericson®, BlackBerry® Torch®, and the like. Examples of tablets include the Apple® iPad®, BlackBerry® PlayBook®, Amazon® Kindle®, Sony® Tablet™, and the like. Examples of phablets include the Samsung® Galaxy® Note®, LG® Optimus Vu®, HTC® One X®, and the like.

In addition to PCDs 108, in some embodiments other devices can be used. For example, in some embodiments, a personal computer (PC) 114, a laptop computer, a cell phone, a wireless phone, a gaming device, a set top box, and/or other electronics devices can be used.

In any case, the PCD 108 or other device is operative to execute an application that facilitates communications (e.g., wireless) with the ordering server 102 and with an analyte meter device (AMD) 110 so as to enable automated tracking and ordering of test strips 112 when needed. The AMD 110 is operative to perform all of the functions of a conventional analyte meter device (e.g., such as the Contour® USB meter manufactured by Bayer Healthcare LLC), and, in addition, to track test strip usage, to track test data, and to communicate (e.g., wireless) with the PCD 108. The AMD 110 includes a port that is adapted to couple to a test strip 112 and measure the analyte characteristic of interest of the fluid sample applied to the test strip 112. As mentioned above, in some embodiments, the system 100 can also optionally include a personal computer (PC) 114 that can connect to the Internet 106 and is operative to communicate with the PCD 108 and/or the AMD 110. The PC 114 can be used to display and communicate information related to the test strip usage and other information such as test data results, status information, special offers, or the like.

In some embodiments, the system 100 can include an optional insurance and/or a healthcare provider server 116 (shown in phantom). This server 116 can be adapted to communicate with the PCD 108, the AMD 110, and/or the other servers 102, 104 to receive information about the user's use of, and test results from, the AMD 110. In some embodiments, regular and consistent use of the AMD 110 can qualify the user for discounts or other promotions from the health insurance company operating the server 116. In this manner, users can be encouraged to take better care of themselves by more carefully monitoring their blood glucose levels, for example. In some embodiments, healthcare providers can use the system 100 to more closely monitor the health of the user. In some embodiments, the healthcare provider can issue a request for test strip usage and results information via the server 116 to the PCD 108 and/or the AMD 110. In some embodiments, this information can be reported to the healthcare provider and/or the health insurance company automatically via the insurance and/or a healthcare provider server 116. As with the other servers 102, 104, the insurance and/or a healthcare provider server 116 can communicate via the Internet 106 or any other practicable network.

Turning to FIG. 2, a front partial cut-away view of an example embodiment of an AMD 110 and an attached test strip 112 is provided. The AMD 110 in the depicted embodiment includes a port that is adapted to receive and configured to couple with the test strip 112. The body 202 of the AMD 110 includes a display 204 and operating controls 206 (e.g., push buttons, switches, and the like). The AMD 110 in the pictured embodiment uses an electrochemical analyte sensor (i.e., test strip 112). However, it would be understood that the invention is equally applicable to other types of test strips 112 such as those that function based upon a color change, e.g., optical analyte sensors.

The AMD 110 also includes a wireless communication facility (WCF) 208 such as, for example, a Zigbee® chipset, a Bluetooth® chipset, a Wi-Fi chipset, or the like. The AMD 110 is controlled by a processor (PRC) 210 which includes memory and an AMD operating program. The processor 210 is operatively coupled to each of the display 204, the operating controls 206, the WCF 208, and the coupling to the test strip 112. The AMD 110 also includes numerous additional practicable features not shown that would be understood to be included in such a device such as a battery/power system.

The AMD operating program stored in the processor memory is adapted to execute on the processor 210 to perform the various methods of the present invention. The AMD operating program includes a number of modules adapted to perform various functions including communicating data to the PCD 108 via the WCF 208, storing test strip tracking information (e.g., usage counts, quantities, test strip lot IDs, usage rates, and the like), determining if a reorder threshold has been reached, testing an analyte on the test strip 112, displaying information on the display 204, receiving control signals from the operating controls 206, and the like. More generally, the AMD operating program is adapted to execute various methods of the invention as described below with reference to FIG. 5.

Turning now to FIG. 3, an example of a PCD 108 is depicted displaying an example PCD application screen display 302 according to embodiments of the present invention. The PCD 108 can include a camera which together with the PCD application can be used to input information via scanning a code or other indicia from a package of test strips. The number of strips in the package may also be manually input in some embodiments. The PCD application can be provided as a downloadable program via an applications store accessible via a built-in application included by the PCD manufacturer as part of the PCD 108. For example, the Apple® iPhone® provides a built-in "App Store" application for finding and downloading applications distributed via the Apple® App Store. The PCD application can include a number of modules adapted to perform various functions including communicating data to the AMD 110, storing test strip tracking information (e.g., usage counts, quantities, test strip lot IDs, usage rates, and the like), determining if a reorder threshold has been reached, displaying information on the display 302, and the like. More generally, the PCD application is adapted to execute various methods of the invention as described below with reference to FIG. 5.

The particular example screen display 302 depicted in FIG. 3 includes a reporting message 304 indicating to the user that that the PCD application has determined additional test strips 112 will soon be needed and that these additional test strips 112 have been automatically ordered. The example screen display 302 also includes a graph 306 indicating the actual (black bars) and predicted (white bars) inventory of test strips 112 over time. Thus, the user can easily see that within a few days, the number of strips would be zero if more strips were not ordered. Numerous additional and alternative screen displays 302 can be used with the present invention and the image shown in FIG. 3 is merely representative of an example screen display 302.

FIG. 4 depicts a representation of an example of a simplified database 400 that can be used in some embodiments of the present invention. In some embodiments, this example database 400 can be stored on the PCD 108 and managed (e.g., populated, accessed, updated, etc.) by the PCD application. In some embodiments, the database 400 can be stored on the AMD 110 and managed by the AMD operating program. In some embodiments, part or a version of the database 400 can be stored on the PCD 108 and part or a version can be stored on the AMD 110. In some embodiments, the database 400 can be stored on and managed by an online server (e.g., 102, 104, 116) or a personal computer 114.

The example database 400 is presented in a table format for illustrative purposes. However, those of ordinary skill would readily understand that many different alternative formats can be used. The example database 400 shown is useful for storing test and test strip data. The database 400 is adapted to include several fields 402, 404, 406, 408, 410, 412, 414 (vertical columns) for each database record or entry 416, 418, 420, 422, 424 (horizontal row).

In some embodiments, the fields can include: a test identification field 402 useful for storing a unique index for referencing each test or test strip used; a test date field 404 useful for storing an indicia representative of the date the test associated with the given entry was performed or the date the test strip associated with the given entry was used; a test time field 406 useful for storing an indicia representative of the time the test associated with the given entry was performed or the time the test strip associated with the given entry was used; a test result field 408 useful for storing an indicia representative of the outcome of the test associated with the given entry; a remaining strip count field 410 useful for storing an indicia representative of the number of test strips the user has in his supply after the test associated with the given entry has been completed; a consumption rate field 412 useful for storing an indicia representative of a running average of the number of test strips per day that the user consumes; an anticipated reorder date field 414 useful for storing an indicia representative of a predicted date upon which the next lot of test strips should be reordered to avoid the user running out of test strips; and the like. Many additional or alternative fields can be included. For example, a test strip lot identification field, a user identification field (where users share a single AMD 110), a test strip cost information field, and the like could also be included in the database 400.

Each entry (horizontal row) 416, 418, 420, 422, 424 of the example database 400 stores information about a unique test and corresponding test strip used. The example database 400 includes many entries however only five representative entries 416, 418, 420, 422, 424 are shown.

The example data shown populating the example database 400 is merely illustrative and is only intended to demonstrate the type and form of information that can be stored. An example scenario is now described to further illustrate the operation of the invention. Entry 416 indicates that the user tested his blood glucose level on May 1, 2012 at 4:09 PM. The level was 93 mg/dl and he had 17 test strips remaining afterward. The remaining strip count field 410 is decremented after each test strip is used. To date, the user had averaged about 4.1 tests per day and based on that rate of testing and the remaining number of strips, the PCD 108 has determined that on May 2, 2012, additional test strips should be ordered.

The next morning, which is May 2, 2012, the PCD 108 has ordered additional test strips as indicated by the new value in the anticipated reorder date field 414 in entry 420. A screen display 302 such as the one depicted in FIG. 3 can be presented to the user. Two days later, at sometime between 7:02 AM and 11:11 AM, a new package of 50 test strips arrived and was scanned by the user with the PCD 108. This is indicated by the updated value in the remaining strip count field 410 in entry 424. Note that in this example, the anticipated reorder date field 414 is updated once the new test strips are ordered. The remaining strip count field 410 is updated once the new test strips actually arrive and have been scanned. In some embodiments, the values in the various fields can be updated at different points in time.

Figure 5:
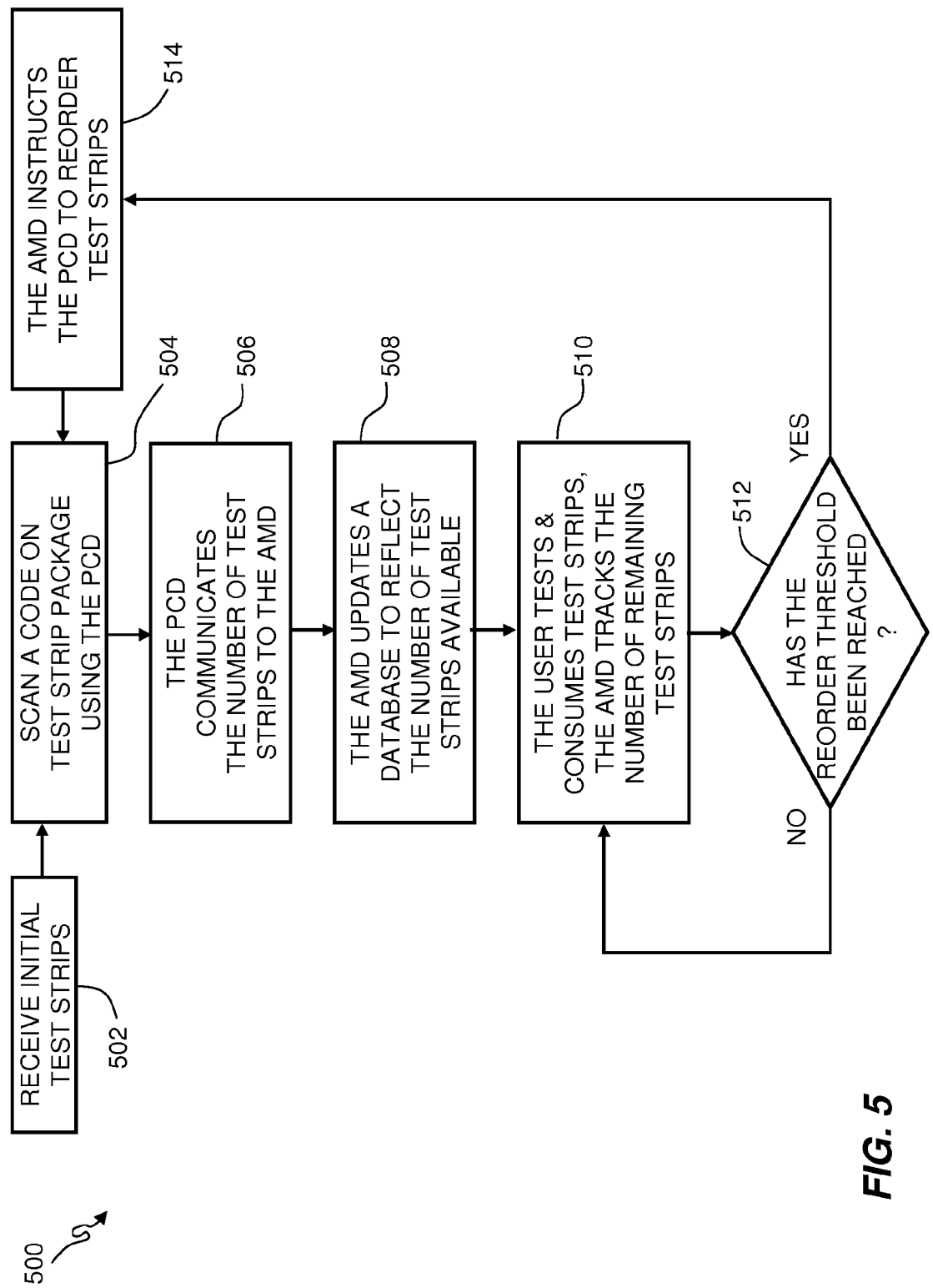
FIG. 5 illustrates a flowchart depicting an example method of automating the re-ordering of test strips according to embodiments.

Turning now to FIG. 5, a flowchart depicting an example method 500 of embodiments of the invention is provided. In step 502, an initial lot of test strips 112 is received. The initial lot can be included with the AMD 110 when the AMD 110 was initially acquired by the user. In some embodiments, the initial lot of test strips 112 can be purchased at a store or via mail order or received from a healthcare provider. Regardless, the user scans a code or other indicia on the package of the test strip lot using the PCD 108 in step 504. The PCD application running on the PCD 108 is adapted to decode the scanned code and determine the number and type of test strips 112 in the package. The number and type of test strips 112 along with other information such as manufacturing date, expiration date, manufacturer identifier, lot number, and the like, can be communicated to the AMD 110 in step 506.

In step 508, the AMD 110 can update a database (e.g., the database 400 depicted in FIG. 4) or another data structure with some or all of the information decoded by the PCD 108 from the test strip package. In some embodiments, some or all of the information can be stored in both or either the PCD 108 and the AMD 110. In step 510, the AMD 110 tracks the use of the test strips 112 and can update the database 400 or other data structure accordingly. In some embodiments, the AMD 110 can communicate the test strip usage (and test result) information to the PCD 108 whenever the two devices are within communication range, able to establish communications, or immediately via the Internet. In some embodiments, a PC 114 can function as a server to keep the information synchronized between the AMD 110 and the PCD 108. In some embodiments, a third-party server 102, 104, 116 can function as a synchronization server to distribute information to the AMD 110 or the PCD 108.

In step 512, a determination is made whether a reorder threshold has been reached. The determination can be made by the AMD 110 based on the number of test strips consumed and the number of test strips at step 506. For example, the AMD 110 can determine that the reorder threshold has been reached if only 16 or fewer test strip remain in the user's supply. In some embodiments, the AMD 110 can consider the rate at which the test strips are used and, for example, determine that the reorder threshold is reached 4 days before the user is expected to run out of test strips.

If the reorder threshold has not been reached, the method 500 returns to step 510 where testing continues. If the reorder threshold has been reached, the method 500 proceeds to step 514 where the AMD 110 instructs the PCD 108 to reorder test strips 112. In some embodiments where the PCD 108 is tracking the use of the test strips, the PCD 108 can reorder test strips 112 on its own without an instruction from the AMD 110. Upon receipt of the reordered test strips 112, flow returns to step 504 and the method 500 continues.

The above method 500 is merely illustrative and many alternative and additional steps are possible. In some embodiments, additional information can be tracked along with the number of test strips. For example, the user's diet, exercise, blood glucose level, and the like can be tracked and stored by the PCD 108 and/or AMD 110. An interface can be provided to enter such additional information and/or the additional information can come from a third-party online application (e.g., Fitday® (http://www.fitday.com/) or the like) or a PC 114 based journaling application. Based on this additional information, recommendations regarding health management can be made. For example, if the AMD 110 determines that the user is following a treatment plan very closely (e.g., adhering to a predefined diet and exercise plan), the AMD 110 can determine that the user only needs to test his blood glucose level three times a day instead of four. The AMD 110 can then suggest the user test his blood less frequently. In some embodiments, the AMD 110 can also adjust the reorder threshold accordingly.

Likewise, if tracking of the additional information indicates that the user's health would benefit from more frequent testing, the AMD 110 can suggest the user test his blood glucose level more frequently and adjust the reorder threshold accordingly. In some embodiments, where the information being tracked indicates a significant change in the user's treatment plan is warranted, the AMD 110 and/or the PCD 108 can contact the user's healthcare provider (e.g., via the healthcare server 116) to alert the healthcare provider of the situation.

In some embodiments, the PCD 108 can track all of the information and the AMD 110 merely reports test strip information (e.g., usage, results, timing, and the like) to the PCD 108. Likewise, in some embodiments, the AMD 110 can track all of the information and the PCD 108 is merely used to scan and order new packages of test strips. In some embodiments, both the PCD 108 and the AMD 110 track the information and in some embodiments, the tracking of the information is done in part by the PCD 108 and part by the AMD 110.

In any case however, the PCD 108 and the AMD 110 include the ability to communicate and provide data updates to each other. The data updates can be triggered by several different methods or a combination of different methods. In some embodiments, a time-based reminder can be used to inform the user that a data transfer is pending and the user should take steps to facilitate the transfer. For example, the display of either or both the PCD 108 and the AMD 110 can present a message to the user to bring the devices within transmission range of each other, to connect either or both to the Internet or to a local area network, to pair them together (e.g., via Bluetooth®), to couple them via a cable (e.g., a USB cable), or the like.

In some embodiments, the PCD 108 and the AMD 110 can be adapted to automatically communicate and perform data transfers whenever the devices are within a certain predefined proximity of each other. In some embodiments, the devices can function in an opportunistic manner and communicate whenever they are able.

In some embodiments, the PCD 108 and the AMD 110 can be triggered to communicate and perform data transfers whenever a healthcare provider and/or and insurance provider issue a request (e.g., via the insurance and/or a healthcare provider server 116) for information. In such embodiments, the user can receive a message via email or text on the PCD 108 instructing him to couple the PCD 108 and the AMD 110.

In some embodiments, the PCD 108 and the AMD 110 can be triggered to communicate and perform data transfers based on certain predefined events. For example, each time a test strip is used, the AMD 110 can attempt to communicate the associated data to the PCD 108. In some embodiments, the AMD 110 may only attempt to communicate the data after, for example, every fifth test. In some embodiments, the PCD 108 can communicate with the AMD 110 whenever a package is scanned or a reorder has been made.

In some embodiments, the PCD 108 and the AMD 110 can be separate devices as discussed above and in some embodiments, the PCD 108 and the AMD 110 can be integrated to different degrees. In some embodiments, the AMD 110 can be implemented as a plug-in module adapted to couple directly to a PCD 108. In such an embodiment, the AMD 110 would only include a hardware interface to the PCD 108 and a port for receiving and activating a test strip. All the remaining functionality including the display, power, controls, etc. can be implemented in the PCD 108. In some embodiments, an AMD 110 can include the communication and camera facilities of a Smartphone or tablet and a separate PCD 108 would not be needed.

In embodiments where the PCD 108 and the AMD 110 are separate devices, the devices can include a wireless or wired channel that is dedicated to communication between the two devices. For example, in some embodiments, the PCD 108 and the AMD 110 can be paired together via a persistent connection (e.g., Bluetooth® or the like). In some embodiments, the PCD 108 and the AMD 110 may not communicate directly at all. In such embodiments, an intermediary computer (e.g., a PC 114) can serve to communicate with each of the PCD 108 and the AMD 110 and make the relevant information available to the respective devices. In some embodiments, the user can manually provide information to the PCD 108 and/or the AMD 110 from information displayed on the AMD 110 and/or the PCD 108. For example, after the PCD 108 is used to scan the test strip package, the PCD 108 can provide the user with instructions directing him to enter information manually into the AMD 110. Likewise, in another example, after the AMD 110 determines the reorder threshold has been reached, the AMD 110 can provide the user with instructions directing him to manually enter information into the PCD 108 which will cause the PCD 108 to reorder test strips. Thus, even when the PCD 108 and the AMD 110 are unable to communicate directly, the system 100 can still be operative to timely reorder test strips.

In some embodiments, the AMD 110 can include additional functionality to facilitate authentication of the test results. For example, the information output by the AMD 110 can be encrypted and include timestamp information, user identification information (e.g., generated based upon blood characteristics, a biometric sensor included within the AMD 110, or the like), test strip identification information (e.g., test strip lot number ID, test strip ID serial number, or the like), test result information, and/or the like. In some embodiments, information transmitted originating from the AMD 110 can include a unique serial number identifying the AMD 110 and other information that can be verified upon receipt of the transmitted information. In this manner, the authenticity of the information can be verified.

In some embodiments, the AMD 110 can include a facility for saving a sample of the fluid being tested. The AMD 110 can include a compartment that is adapted to cut-off and store the portion of the test strip 112 that includes the fluid sample. The AMD 110 can instruct the user to insert the relevant portion of the test strip into the compartment and the strip can be automatically cut. Thus, in some embodiments, the actual sample that generated a particular result can be retained and associated with the respective test results. A healthcare provider can be alerted to the presence of the stored sample and if desired, the AMD 110 with the sample can be sent to the provider.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The foregoing description discloses only example embodiments of test strips, AMDs, PCDs, PCD applications, other apparatus, systems including the same, and methods of the invention. Modifications of the above-disclosed embodiments, which fall within the scope of the invention, will be readily apparent to those of ordinary skill in the art. Accordingly, while the present invention has been disclosed in connection with example embodiments thereof, it should be understood that other embodiments may fall within the scope of the invention, as defined by the following claims.

The invention claimed is:

1. An automated analyte meter test strip ordering system, comprising:

an analyte meter device including a first processor with a first memory storing first instructions and a wireless communications facility, the first processor programmed to execute the first instructions to direct the first processor to use test strips to measure a characteristic of an analyte, to track a quantity of the test strips used, and to transmit information regarding the tracked quantity of the test strips used;

a package of test strips including a plurality of test strips and a machine-readable indicia on an exterior surface of the package, the indicia representative of at least an initial number of test strips in the package; and a personal communications device, separate and distinct from the analyte meter device, the personal communications device including a second processor with a second memory storing second instructions, an indicia reading device, and a communications transceiver, the second processor programmed to execute the second instructions to direct the second processor to use the indicia reading device to read input information from the indicia on the package of test strips, to use the communications transceiver to communicate with the analyte meter device to receive the information regarding the tracked quantity of the test strips used, to determine when to order additional test strips based on the information received from the analyte meter device and the indicia on the package of test strips, and to use the communications transceiver to order additional test strips from an ordering server, wherein the indicia reading device includes a camera within the personal communications device operable to photograph the indicia via capturing an image of the indicia from the package and decoding the photographed indicia.

2. The system of claim 1 further comprising an ordering server operative to communicate with the personal communications device and to receive a test strip order from the personal communications device.

3. The system of claim 1 wherein the personal communications device further includes additional second instructions stored in the second memory, the additional second instructions directing the second processor to communicate the decoded indicia using the communications transceiver to the analyte meter device.

4. The system of claim 1 wherein the personal communications device further includes additional second instructions stored in the second memory, the additional second instructions directing the second processor to track a rate of test strip usage in the analyte meter device.

5. The system of claim 1 wherein the analyte meter device further includes additional first instructions stored in the first memory, the additional first instructions directing the first processor to track a rate of test strip usage in the analyte meter device.

6. The system of claim 1 wherein the analyte meter device further includes additional first instructions stored in the first memory, the additional first instructions directing the first processor to determine that a reorder threshold has been reached and to communicate that the reorder threshold has been reached using the wireless communications facility to the personal communications device.

* * * * *